United States Patent [19]

France

[11] 4,346,601
[45] Aug. 31, 1982

[54] TESTING GLASS FIBRES

[75] Inventor: Paul W. France, Suffolk, England

[73] Assignee: The Post Office, London, England

[21] Appl. No.: 179,085

[22] Filed: Aug. 18, 1980

[51] Int. Cl.$^3$ .............................................. G01N 3/08
[52] U.S. Cl. ..................................... 73/829; 73/849; 73/160
[58] Field of Search .......................... 73/829, 849, 160

[56] References Cited

U.S. PATENT DOCUMENTS 2,435,266  2/1948  Brillhart ................................. 73/829
4,286,469  9/1981  Trias ...................................... 73/829

Primary Examiner—Anthony V. Ciarlante
Attorney, Agent, or Firm—Kemon & Estabrook

[57] ABSTRACT

A method of proof testing an optical glass fibre by pulling it around a free roller whose radius is sufficiently small to impart the strain necessary to detect fibres whose surface or near surface flaws weaken the fibre below a required strength. Proof testers are disclosed incorporating, single rollers, a set of three parallel rollers and a jig holding four sets of three rollers. Proof testers incorporating the extra rollers whose axes are at different angles are shown to more thoroughly explore the surface of the fibre for cracks.

12 Claims, 7 Drawing Figures

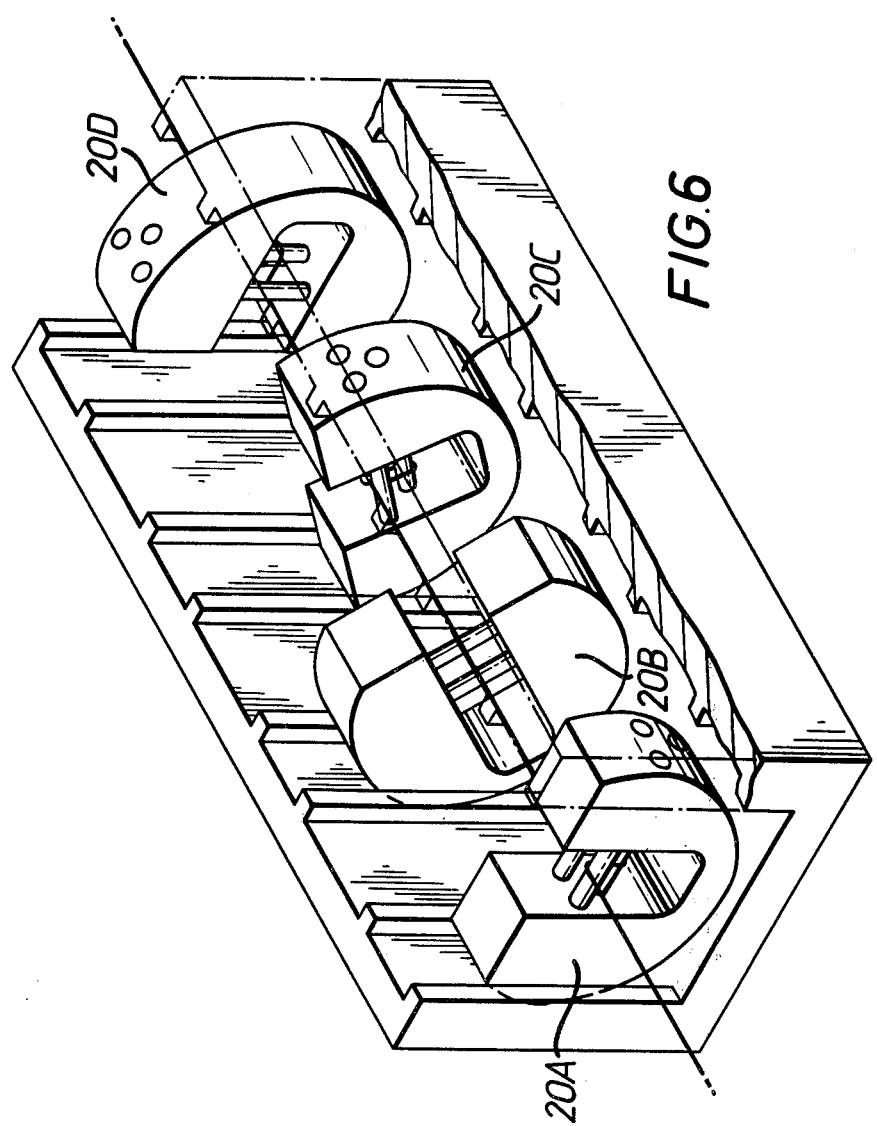

TESTING GLASS FIBRES

This invention relates to testing glass fibres. In particular the invention relates to the proof testing of optical glass fibres, to detect flaws in the glass and thus the suitability of the fibres for use as dielectric waveguides in optical communications systems.

Short gauge length tensile testing can yield much information concerning the flaw distribution in optical glass fibres of relatively short length but the information cannot be reliably extrapolated to the kilometer lengths necessary in optical fibre cables.

Proof testing is a way of more fully characterising long samples and can be used to ensure guaranteed strength for a given length of fibre, e.g. greater than that strength expected in subsequent cabling and service operations, and to ensure a minimum lifetime for a fibre in a stressed condition.

Convention proof testing apparatus operates by applying tensile strain to a fibre, which is wound between two capstans. One capstan is fitted with constant torque motor which determines the load on the fibre whilst the other drives the fibre at a constant speed.

This method can impart a strain of up to about 1% to the fibre, but suffers from the disadvantage that the tension necessary (about 600 grams) to impart this strain causes a considerable pressure between the fibre and the capstan and hence damage to the fibre surface even through its thin protective coating.

It is desirable to impart a high strain (above 1%) in the fibre without the risk of surface damage and the present invention aims to achieve this requirement.

According to a first aspect of the present invention there is provided a method of proof testing a glass fibre to detect fibres having a strength greater than a predetermined value, the method comprising moving the fibre along a path in which it is bent over the surface of a roller which is free to rotate, the roller having a diameter such that tensile strain induced by bending in the surface of said optical fibre corresponds to the said predetermined value of strength, the fibres being drawn around said roller so that successive portions of said fibre are subjected to the tensile strain induced by bending. Because the strain is induced by bending, the tensile load in the fibre can be very small (~30 gms) and hence high proof-test levels can be attained without damage to the fibre.

The tensile strain to which the surface of said fibre is subjected may be greater than 1%. The fibre may be passed through a set of three rollers which are arranged such that said fibre is bent in a first sense about a first roller, then in a second sense opposite to said first sense about a second roller, and then in said first sense about a third roller. The rollers may be arranged so that the tensile strain induced by bending is maintained for substantially 90° about said first roller, for substantially 180° about said second roller, and for substantially 90° about said third roller.

The fiber may be passed through n sets of three rollers, the rollers of each set being orientated such that 2xn axial lines on the surface of said fibre are subjected to a maximum value of said tensile strain induced by bending. n may be equal to 4, and the 4 sets of rollers located so that said 8 lines are equi-angularly spaced about the circumference of said fibre.

The fibre may be a plastics sheathed optical fibre.

According to a second aspect of the present invention there is provided apparatus for proof-testing glass fibres to detect glass fibres having a strength greater than a predetermined value, said apparatus comprising n sets of m rollers, where n and m are greater than 1, each roller being free to rotate, the rollers of each set of rollers being mounted in a respective one of n support means, and means for holding said n support means at predetermined angles to each other, the arrangement being such that when a fibre is drawn through said sets of rollers maximum strain is induced in the fibre at positions substantially evenly distributed about the circumference of said fibre.

The apparatus may have three rollers and the support means may be a block, the rollers being mounted so that the axes of two rollers lie in a plane and are separated by a gap, the third roller being mounted parallel to, but out of said plane, and substantially midway between two planes which pass one through each axis of said two rollers in a direction normal to said one plane.

The apparatus may have a support means comprising a U-shaped block and the rollers may be located in the gap between the limbs of the block, each roller having a bearing means in each limb of the block.

Means for holding the blocks may comprise an open ended box having channels on its inner wall for receiving and holding said U-shaped blocks in predetermined orientations.

The invention will be described now by way of example only with particular reference to the accompanying drawings in which:

FIG. 6 is a perspective view of a proof testing apparatus having four sets of three rollers, each set mounted at 45° to two other sets.

Figure 1:
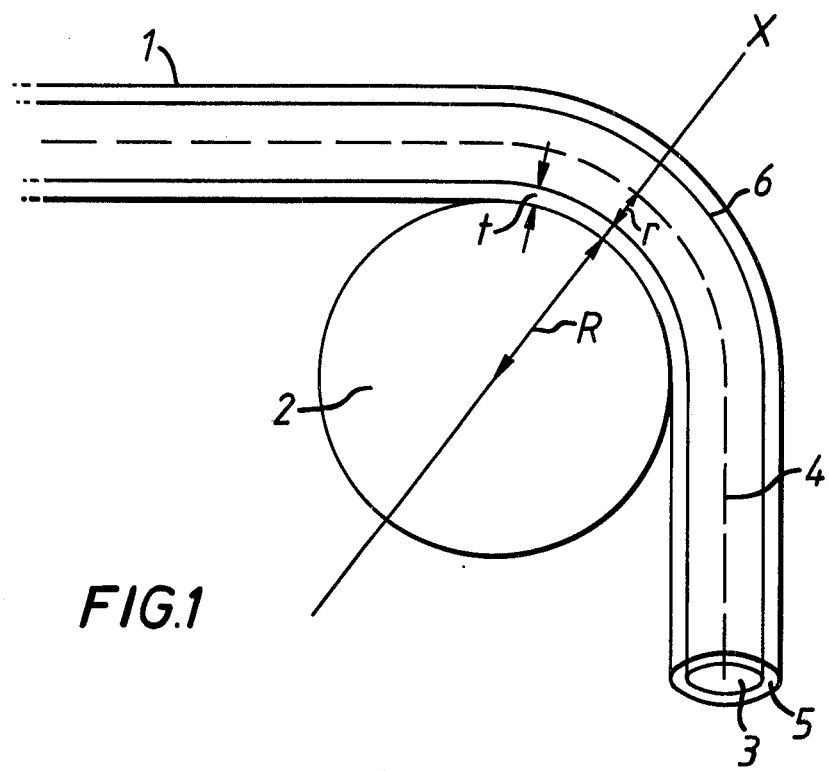
FIG. 1 shows a part sectional view of an optical glass fibre being pulled around a roller.

The present technique will be described initially with reference to FIG. 1. In this Figure a plastics coated optical fibre 1 is shown being pulled along a path which passes round part of the circumference of a roller 2 of radius R. The plastics coated fibre 1 comprises a central glass portion 3 having a generally circular cross-section of radius and an outer protective coating 5 of thickness t. The fibre 1 is pulled around the roller 2 under sufficient tension to ensure a good contact between the plastics coated fibre 1 and the roller 2 for about a quarter of a revolution of the roller 2. The axis 4 of the fibre 1 can be seen to be curved into a circular path whose radius is $R+t+r$ whilst the outer surface of the central glass portion 3 is under strain being curved into a path of radius $R+t+2r$. As the fibre 1 is passed round the roller 2 the central glass portion 3 is progressively subjected to a strain whose maximum can be shown to be:

$$T_{max} = (r)/(R+t+r) \times 100\%$$

The strain imparted to a fibre 1 by the roller 2 is therefore inversely proportional to the radius R of the roller 2 and the strain to which a fibre is to be proof tested determines the dimension of the roller to be used.

Figure 2:
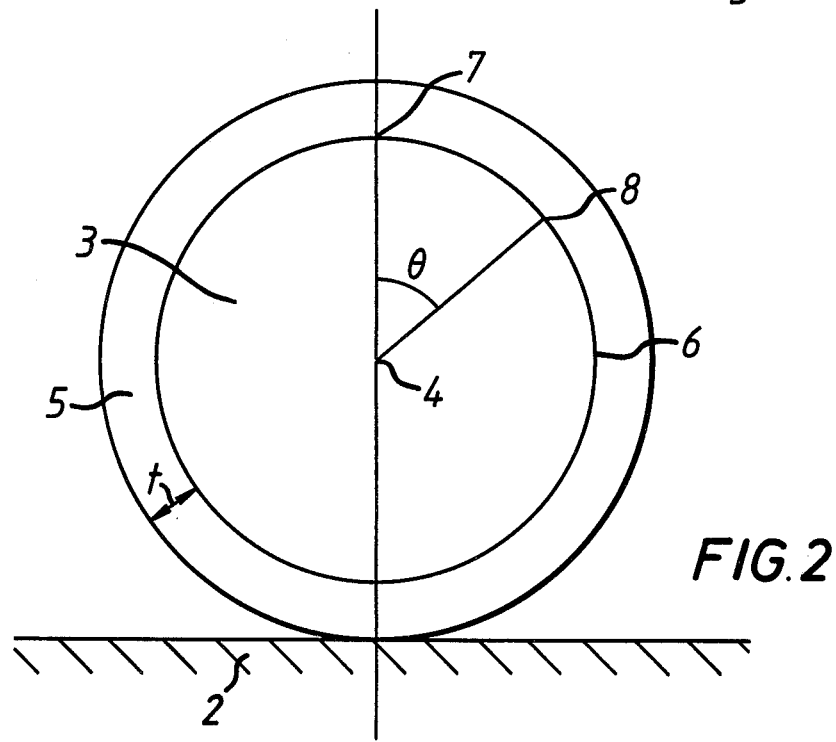
FIG. 2 shows a section along the line X—X of FIG. 1.

Referring now to FIG. 2 it will be appreciated that the strain imparted varies with position within the central glass portion 3. The maximum strain T max occurs only along an axial line through the point 7 at a radially outermost position on the surface 6 of the glass portion 3. On any other axial line such as that through the point 8 on the surface of the glass portion 3 the strain will be $T = T \max \cos \theta$, where $\theta$ is the angle between a radius to the point 7 and a radius to the point 8. The strain within the glass portion 3 will be proportional to its radius at that point. In the present technique a fibre is proof tested by pulling it along a path which extends around a roller which is free to rotate as shown in FIG. 1. The diameter of the roller is such that the tensile strain induced by bending in the surface of the optical fibre corresponds to a predetermined value of strength which the fibre is required to have. It may be thought disadvantageous that only points on the surface of the glass are subjected to maximum strain but as the majority of fibre flaws are Griffith microcracks which lie on or near the surface, the technique will detect the majority of flaws.

Figure 3:
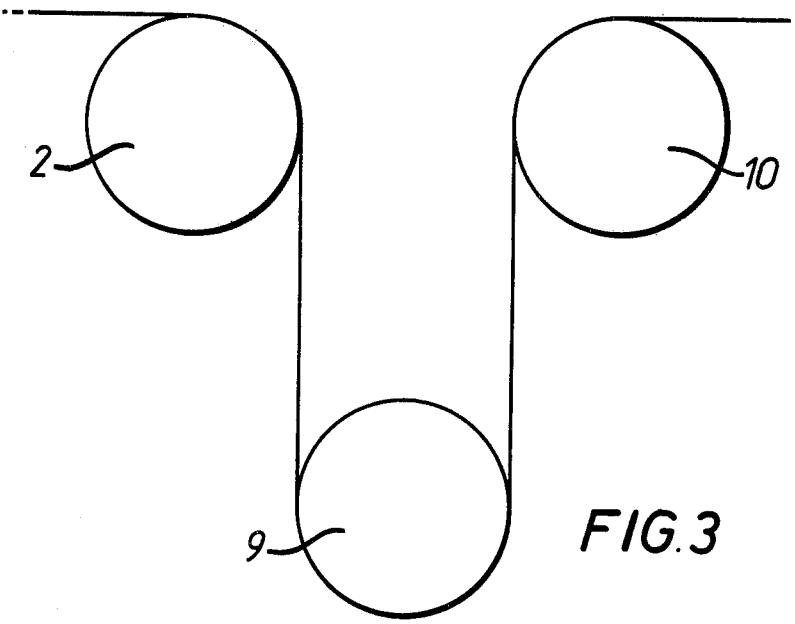
FIG. 3 shows a sectional view of a set of three proof testing rollers as used in accordance with the invention.

FIG. 3 illustrates how it is possible to subject more than one line of the surface of the glass portion 3 to the maximum available strain T max by passing the fibre around another roller 9. This causes a part of the fibre diametrically opposite the line 7 to be subjected to the maximum strain and does so for about half a revolution of the roller. A third roller 10 is arranged such that the line 7 is subjected again to the same strain T max for about a quarter of a revolution and serves in addition to align the fibre 1 as it enters and leaves the set of three rollers 2, 9 and 10.

Figure 4:
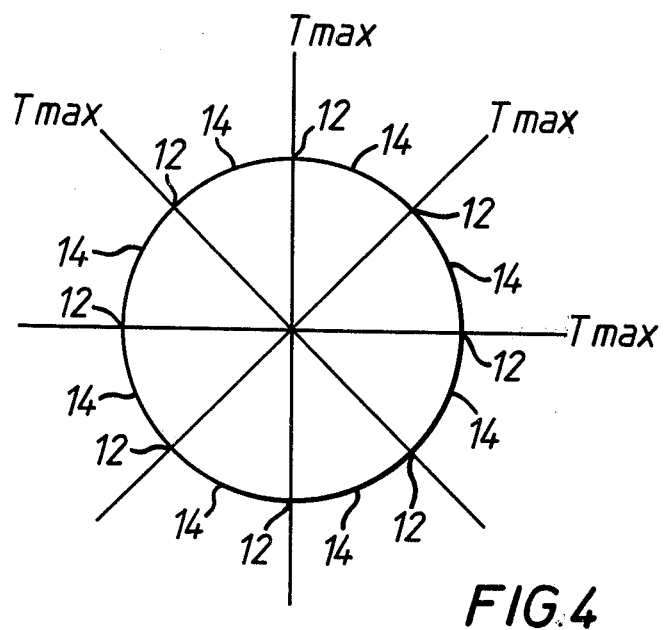
FIG. 4 illustrates in section an optical glass fibre tested in accordance with the invention.

Thus it is possible to proof test a long length of glass fibre by passing it along a U-shaped path over two and under one of the set of three rollers as shown in FIG. 3. Again the radius of the rollers is determined by the testing specification and the tension must be adequate to ensure good roller to fibre contact. However if only a single set of three rollers is used much of the surface of the fibre does not suffer the maximum strain and points on the surface along one pair of diametrically opposite lines pass through having suffered no strain. This effect can be reduced significantly be repeatedly passing the fibre through the set of rollers or preferably by mounting several sets of rollers so that the roller axes in the various sets are at angles to each other. For example four sets of rollers can be employed, the sets being spaced along a linear path extending at right angles to the roller axes. The sets of rollers are oriented so that, when viewed along the linear path, the axes of the rollers of the second set are at 45° in one sense to those of the first set, the axes of the rollers of the third set are at 45° in the opposite sense to those of the first set, and the axes of the rollers of the fourth set are at 90° to those of the first set. If a fibre is passed through four sets of rollers arranged in this manner the maximum strain T max is exerted along each of eight lines on the surface of the fibre. This is illustrated in FIG. 4 in which the eight lines of maximum strain extend linearly along the surface of the glass portion 3 through the eight points 12. In this way not only is a much greater area of the glass surface fully strained but also the minimum strain that is experienced on the surface of the glass along the lines 14 in FIG. 4, is kept as high as practicable and can be shown in this case to be greater than 90% of T max.

Figure 5:
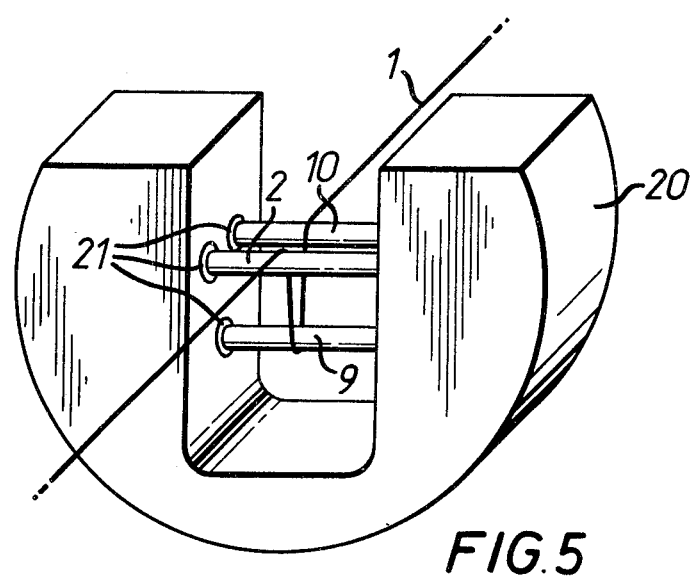
FIG. 5 shows a set of three rollers mounted in a block in accordance with the invention.

One way in which the rollers can be mounted is shown in FIG. 5. A set of three stainless steel rollers 2, 9 and 10 is mounted as shown between the limbs of a generally U-shaped block 20. The ends of each roller are mounted in bearings 21 so that the rollers can rotate freely. The outer periphery of the block 20 is generally circular in cross-section.

FIG. 6 shows how four blocks 20A, 20B, 20C, 20D can be mounted in an open ended box 22 to produce the regions of maximum tension illustrated in FIG. 4. Each block is held within respective channels 23 formed on the inner surface of the side-walls of the box. By virtue of the generally circular shape of the outer periphery of each block, the blocks can be rotated within the box so that they can be set to the correct relative orientation to produce the required region of maximum tension illustrated in FIG. 4.

Figure 7:
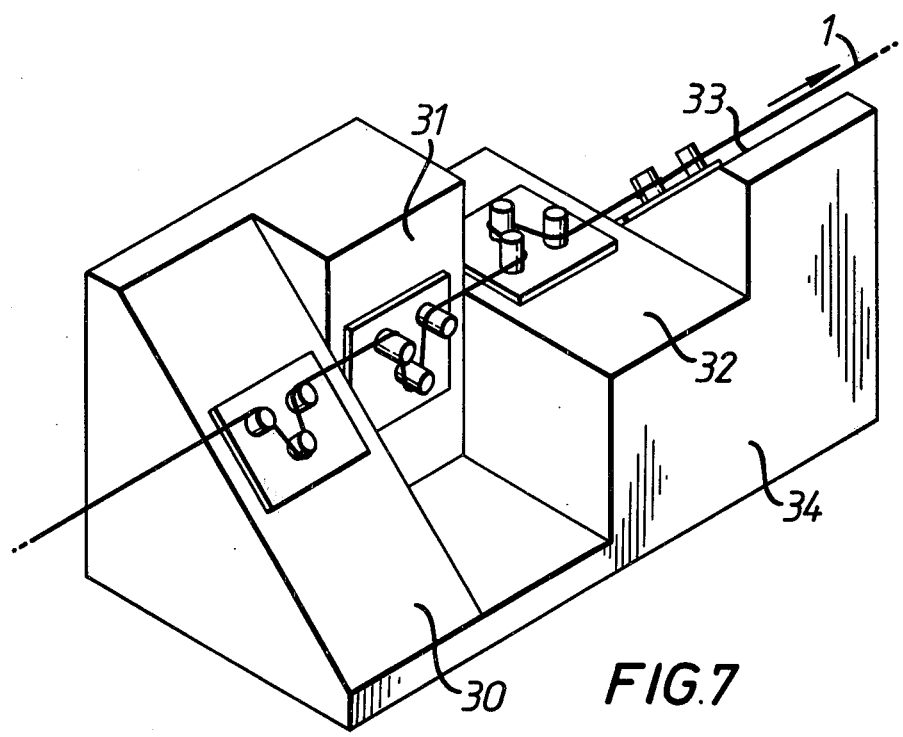
FIG. 7 is a perspective view of an alternative form of proof testing apparatus in accordance with the present invention.

FIG. 7 illustrates an alternative way of mounting the rollers. The four sets of rollers are mounted on surfaces 30, 31, 32, 33 machined on a block 34. The surface 30 is inclined at 45° to the surface 31, the surface 32 at 90° to the surface 31 and the surface 33 at 90° to the surface 31. The rollers have the same relative orientations as in the arrangement of FIG. 6 so that a fibre 1 drawn through the rollers is subjected to the strains illustrated in FIG. 4. The arrangement of FIG. 7 has the advantage that it is easier to thread the fibre around the rollers since they are mounted in bearings at one end only the other end being free. It should be noted that the rollers are free to rotate so that there is little or no possibility of frictional damage caused by fibre slippage on a roller.

The proof testing apparatus can be located at any convenient position. For example it could be located between the constant speed capstan and the take-off drum of the fibre pulling and coating apparatus described in "Fibre and Integrated Optics" Volume 2 Number 3–4, pages 267 to 285 (1979) and shown in FIG. 2 thereof. This would allow optical fibres to be proof-tested as they are produced.

I claim:

1. A method of proof testing a glass fibre to detect fibres having a strength greater than a predetermined value, the method comprising moving the fibre along a path in which it is bent over the surface of a roller which is free to rotate, the roller having a diameter such that tensile strain induced by bending in the surface of said optical fibre corresponds to the said predetermined value of strength, the fibres being drawn around said roller so that successive portions of said fibre are subjected to the tensile strain induced by bending.

2. A method of proof testing a glass fibre as claimed in claim 1 wherein said tensile strain is greater than 1%.

3. A method of proof testing a glass fibre as claimed in claim 1 or claim 2 wherein said fibre is passed through a set of three rollers which are arranged such that said fibre is bent in a first sense about a first roller, then in a sense opposite to said first sense about a second roller and then in said first sense about a third roller.

4. A method as claimed in claim 3 wherein said rollers are arranged so that said tensile strain induced by bending is maintained through substantially 90° about said first roller, through substantially 180° about said second roller, and through substantially 90° about said third roller.

5. A method as claimed in claim 3 wherein said fibre is passed through n sets of three rollers, the rollers being orientated such that 2xn axial lines on said surface of said fibre are subjected to a maximum value of said tensile strain induced by bending.

6. A method as claimed in claim 5 where n is equal to 4, and said 4 sets of rollers are located so that said 8 lines are equi-angularly spaced about the circumference of said fibres.

7. A method as claimed in claim 6 wherein the fibre is a glass optical fibre having a plastics sheath.

8. Apparatus for proof-testing glass fibres to detect glass fibres having a strength greater than a predetermined value, said apparatus comprising n sets of m rollers, where n and m are greater than 1, each roller being free to rotate, the rollers of each set of rollers being mounted in a respective one of n support means so that the rotational axes of the rollers in each set are parallel, and means for holding said n support means such that a plane extending perpendicularly through the rotational axes of the rollers of any one set is inclinded to similar planes through the rotational axis of the other sets of rollers, the arrangement being such that when a fibre is drawn through said sets of rollers maximum strain is induced in the fibre at positions substantially evenly distributed about the circumference of said fibre.

9. Apparatus as claimed in claim 8 where m equals 3 and said support means is a block, said rollers of each set being mounted so that the axes of two rollers lie in a plane and are separated by a gap and the third roller is mounted parallel to, but out of said plane, and substantially midway between two planes which pass one through each axis of said two rollers in a direction normal to said one plane.

10. Apparatus as claimed in claim 8 or claim 9 wherein said support means is a U-shaped block and the rollers are located in the gap between the limbs of the block, each roller having a bearing means in each limb of the block.

11. Apparatus as claimed in claim 10 including means for holding said blocks comprising an open ended box having channels on its inner walls for receiving and holding said U-shaped blocks in predetermined orientations.

12. Apparatus as claimed in claim 11 wherein the outer periphery of said U-shaped blocks have a generally circular cross sectional shape with a segment removed, and a gap cut into the resultant shape centred on a diameter intersecting the segment chord at 90°, whereby said U-shaped blocks can be rotated within said channels in said open ended box.

* * * * *